(12) United States Patent
Wigbers et al.

(10) Patent No.: US 9,139,511 B2
(45) Date of Patent: Sep. 22, 2015

(54) PROCESS FOR HYDROGENATING NITRILES

(75) Inventors: Christof Wilhelm Wigbers, Mannheim (DE); Christoph Müller, Mannheim (DE); Wolfgang Mägerlein, Mannheim (DE); Petr Kubanek, Mannheim (DE); Thomas Heidemann, Viernheim (DE); Johann-Peter Melder, Böhl-Iggelheim (DE); Thomas Krug, Worms (DE); Oliver Bey, Niederkirchen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/427,388

(22) Filed: Mar. 22, 2012

(65) Prior Publication Data

US 2012/0245390 A1  Sep. 27, 2012

Related U.S. Application Data

(60) Provisional application No. 61/466,016, filed on Mar. 22, 2011.

(51) Int. Cl.
*C07C 209/00* (2006.01)
*C07C 209/48* (2006.01)

(52) U.S. Cl.
CPC .................................. *C07C 209/48* (2013.01)

(58) Field of Classification Search
None
See application file for complete search history.

(56) References Cited

U.S. PATENT DOCUMENTS

| | | | | |
|---|---|---|---|---|
| 5,536,691 | A * | 7/1996 | Breitscheidel et al. | 502/213 |
| 7,572,508 | B2 * | 8/2009 | Lutz et al. | 428/423.1 |
| 2002/0058841 | A1 * | 5/2002 | Ansmann et al. | 564/415 |
| 2009/0069590 | A1 | 3/2009 | Eberhardt et al. | |

FOREIGN PATENT DOCUMENTS

| | | | |
|---|---|---|---|
| EP | | 449089 A1 | 10/1991 |
| WO | WO-2007/128803 A1 | | 11/2007 |

OTHER PUBLICATIONS

European Search Report, EP 11159147, dated Aug. 26, 2011.

* cited by examiner

*Primary Examiner* — Clinton Brooks
(74) *Attorney, Agent, or Firm* — Drinker Biddle & Reath LLP

(57) ABSTRACT

The present invention relates to a process for hydrogenating nitriles by means of hydrogen in the presence of a catalyst in a reactor, where the catalyst is arranged in a fixed bed, wherein the cross-sectional loading in the reactor is in the range from 5 kg/(m² s) to 50 kg/(m² s). The present invention further relates to a process for preparing downstream products of isophoronediamine (IPDA) or N,N-dimethylaminopropylamine (DMAPA) from amines prepared according to the invention.

13 Claims, No Drawings

PROCESS FOR HYDROGENATING NITRILES

CROSS-REFERENCE TO RELATED APPLICATIONS

This application claims the benefit of U.S. Provisional Application 61/466,016, filed Mar. 22, 2011 which is incorporated by reference.

BACKGROUND OF THE INVENTION

The present invention relates to a continuous process for hydrogenating nitriles by means of hydrogen in the presence of a catalyst in a reactor, where the catalyst is arranged in a fixed bed, wherein the cross-sectional loading in the reactor is in the range from 5 kg/(m² s) to 50 kg/(m² s).

The present invention further relates to a process for preparing downstream products of isophoronediamine (IPDA) or N,N-dimethylaminopropylamine (DMAPA) from amines prepared according to the invention.

In the hydrogenation of nitriles to form the corresponding amines, it is frequently necessary to achieve a high conversion of the nitriles used, since unreacted or only partially reacted nitriles are difficult to separate off, can undergo secondary reactions and can lead to undesirable properties such as odor and discoloration in subsequent applications. Furthermore, it is frequently desirable to achieve a high selectivity in respect of the formation of primary amines from primary nitriles and to avoid the formation of secondary and tertiary amines.

The hydrogenation of nitriles is generally carried out by catalytic hydrogenation over noble metals such as Pt, Pd or rhodium or Co and Ni catalysts (see, for example, "Amines, Aliphatic", Ullmann's Encyclopedia of Industrial Chemistry, Published Online: 15 Jun. 2000, DOI: 10.1002/14356007.a02_001).

The process is usually carried out in the suspension mode or in a fixed-bed reactor.

In the suspension mode, the catalyst used has to be separated off from the reaction mixture in order to make an economical process possible. The separation is associated with a process engineering outlay.

When catalysts based on Co, Ni or Cu are used, very high temperatures and pressures are generally necessary in the hydrogenation in a fixed bed in order to reduce the formation of secondary and tertiary amines which can be formed by reaction of primary amine with partially hydrogenated nitrile (=imine intermediate).

For example, EP-449089 discloses the hydrogenation of isophoronenitrile to isophoronediamine at 250 bar and WO 2007/128803 describes the hydrogenation of N,N-dimethylaminopropionitrile (DMAPN) to N,N-dimethylaminopropylamine (DMAPA) at 180 bar.

These drastic reaction conditions can increase the formation of other undesirable by-products and require a high outlay for materials and to ensure safety.

DETAILED DESCRIPTION OF THE INVENTION

It was an object of the present invention to provide a fixed-bed process for hydrogenating organic nitrile compounds, which makes it possible to use hydrogenation catalysts, in particular catalysts comprising Cu, Co and Ni, under relatively mild reaction conditions, i.e., in particular, relatively low pressures and/or temperatures. A further objective of the present invention was to provide a fixed-bed process in which high yields and selectivities can be achieved in the hydrogenation of nitriles and which is, in addition, economical to carry out.

In particular, the formation of secondary and tertiary amines as can be formed, for example, by reaction of unreacted amine with partially hydrogenated nitrile (=imine intermediate) according to scheme 1 should be reduced.

Scheme 1:

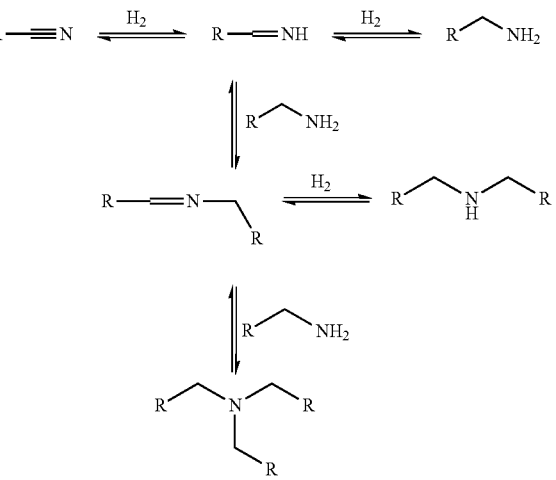

According to the invention, the object is achieved by a continuous process for hydrogenating nitriles by means of hydrogen in the presence of a catalyst in a reactor, where the catalyst is arranged in a fixed bed, wherein the cross-sectional loading in the reactor is in the range from 5 kg/(m² s) to 50 kg/(m² s).

Nitriles are hydrogenated in the process of the invention.

Preference is given to using aliphatic mononitriles, dinitriles and/or trinitriles (linear or branched) having from 1 to 30, in particular from 2 to 18 or from 2 to 8, carbon atoms or cycloaliphatic mononitriles and dinitriles having from 6 to 20, in particular from 6 to 12, carbon atoms or alpha-, beta- or omega-aminonitriles or alkoxynitriles having from 1 to 30, in particular from 2 to 8, carbon atoms in the process of the invention.

Preference is also given to using aromatic nitriles having from 6 to 18 carbon atoms. The abovementioned mononitriles, dinitriles or trinitriles can be monosubstituted or multiply substituted.

Particularly preferred mononitriles are acetonitrile for preparing ethylamines, propionitrile for preparing propylamines, butyronitrile for preparing butylamines, lauronitrile for preparing laurylamine, stearyl nitrile for preparing stearylamine, N,N-dimethylaminopropionitrile (DMAPN) for preparing N,N-dimethylaminopropylamine (DMAPA) and benzonitrile for preparing benzylamine.

Particularly preferred dinitriles are adiponitrile (ADN) for preparing hexamethylenediamine (HMD) and/or 6-aminocapronitrile (ACN), 2-methylglutaronitrile for preparing 2-methyl-glutarodiamine, succinonitrile for preparing 1,4-butanediamine and suberic dinitrile for preparing octamethylenediamine.

Particularly preferred cyclic nitriles are isophoronenitrilimine (IPNI) and/or isophoronenitrile (IPN) for preparing isophoronediamine and isophthalonitrile for preparing meta-xylylenediamine.

Particularly preferred β-aminonitriles are aminopropionitrile for preparing 1,3-diaminopropane or addition products of alkylamines, alkyldiamines or alkanolamines onto acrylonitrile. Thus, addition products of ethylenediamine and acrylonitrile can be converted into the corresponding diamines. For example, 3-(2-aminoethyl)aminopropionitrile can be converted into 3-(2-amino-ethyl)aminopropylamine and 3,3'-(ethylenediimino)bispropionitrile or 3-[2-(3-aminopropylamino)-ethylamino]propionitrile can be converted into N,N'-bis(3-aminopropyl)ethylenediamine.

Particularly preferred ω-aminonitriles are aminocapronitrile for preparing hexamethylenediamine.

Further particularly preferred α-nitriles, known as "extender nitriles" are iminodiacetonitrile (IDAN) for preparing diethylenetriamine and aminoacetonitrile (AAN) for preparing ethylenediamine (EDA) and diethylenetriamine (DETA).

A preferred trinitrile is trisacetonitrilamine.

Very particular preference is given to using N,N-dimethylaminopropionitrile (DMAPN) for preparing N,N-dimethylaminopropylamine (DMAPA), adiponitrile (ADN) for preparing hexamethylenediamine (HMD) or 6-aminocapronitrile (6-ACN) and HMD and isophoronenitrilimine for preparing isophoronediamine in the process of the invention.

In a particularly preferred embodiment, N,N-dimethylaminopropionitrile (DMAPN) is used for preparing N,N-dimethylaminopropylamine (DMAPA) in the process of the invention.

In a further particularly preferred embodiment, isophoronenitrilimine is used for preparing isophoronediamines in the process of the invention and in a further particularly preferred embodiment adiponitrile (ADN) is used for preparing hexamethylenediamine (HMD) or for preparing 6-aminocapronitrile (6-ACN) and HMD.

As reducing agent, it is possible to use hydrogen or a hydrogen-comprising gas. Technical-grade hydrogen is generally used. The hydrogen can also be used in the form of a hydrogen-comprising gas, i.e. in admixture with other inert gases such as nitrogen, helium, neon, argon or carbon dioxide. As hydrogen-comprising gases, it is possible to use, for example, reformer offgases, refinery gases, etc, if and insofar as these gases do not comprise any catalyst poisons for the hydrogenation catalysts used, for example CO. However, preference is given to using pure hydrogen or essentially pure hydrogen in the process, for example hydrogen having a content of more than 99% by weight of hydrogen, preferably more than 99.9% by weight of hydrogen, particularly preferably more than 99.99% by weight of hydrogen, in particular more than 99.999% by weight of hydrogen.

In the process of the invention for preparing amines by reduction of nitriles, the hydrogenation can optionally be carried out with addition of ammonia. Pure ammonia is preferably used in the process, preferably ammonia having a content of more than 99% by weight of ammonia and particularly preferably more than 99.9% by weight of ammonia.

As catalysts for hydrogenating the nitrile function to the corresponding amine, it is possible to use, in particular, catalysts which comprise one or more elements of the 8th transition group of the Periodic Table (Fe, Co, Ni, Ru, Rh, Pd, Os, Ir, Pt), preferably Fe, Co, Ni, Ru or Rh, particularly preferably Co or Ni, as active component. A further preferred active component is Cu.

The abovementioned catalysts can be doped in the usual way with promoters, for example chromium, iron, cobalt, manganese, molybdenum, titanium, tin, metals of the alkali metal group, metals of the alkaline earth metal group and/or phosphorus.

As catalysts, preference can be given to using skeletal catalysts (also referred to as Raney® type, hereinafter also: Raney catalyst) which are obtained by leaching (activating) an alloy of hydrogenation-active metal and a further component (preferably Al). Preference is given to using Raney nickel catalysts or Raney cobalt catalysts.

Furthermore, supported Pd or Pt catalysts are preferably used as catalysts. Preferred support materials are activated carbon, $Al_2O_3$, $TiO_2$, $ZrO_2$ and $SiO_2$.

In a very preferred embodiment, catalysts produced by reduction of catalyst precursors are used in the process of the invention.

The catalyst precursor comprises an active composition which comprises one or more catalytically active components, optionally promoters and optionally a support material.

The catalytically active components are oxygen-comprising compounds of the above-mentioned metals, for example the metal oxides or hydroxides thereof, e.g. CoO, NiO, CuO and/or mixed oxides thereof.

For the purposes of the present patent application, the term "catalytically active components" is used for abovementioned oxygen-comprising metal compounds but is not intended to apply that these oxygen-comprising compounds are themselves catalytically active. The catalytically active components generally display catalytic activity in the reaction according to the invention only after reduction.

Particular preference is given to catalyst precursors such as
the oxide mixtures which are disclosed in EP-A-0636409 and before reduction with hydrogen comprise from 55 to 98% by weight of Co, calculated as CoO, from 0.2 to 15% by weight of phosphorus, calculated as $H_3PO_4$, from 0.2 to 15% by weight of manganese, calculated as $MnO_2$, and from 0.2 to 5.0% by weight of alkali metal, calculated as $M_2O$ (M=alkali metal), or oxide mixtures which are disclosed in EP-A-0742045 and before reduction with hydrogen comprise from 55 to 98% by weight of Co, calculated as CoO, from 0.2 to 15% by weight of phosphorus, calculated as $H_3PO_4$, from 0.2 to 15% by weight of manganese, calculated as $MnO_2$, and from 0.05 to 5% by weight of alkali metal, calculated as $M_2O$ (M=alkali metal), or oxide mixtures which are disclosed in EP-A-696572 and before reduction with hydrogen comprise from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$, for example the catalyst disclosed in loc. cit., page 8, having the composition 31.5% by weight of $ZrO_2$, 50% by weight of NiO, 17% by weight of CuO and 1.5% by weight of $MoO_3$, or oxide mixtures which are disclosed in EP-A-963 975 and before reduction with hydrogen comprise from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar ratio of Ni:Cu being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or MnO$_2$, and no oxygen-comprising compounds of molybdenum, for example the catalyst A disclosed in loc. cit., page 17, having the composition 33% by weight of Zr, calculated as ZrO$_2$, 28% by weight of Ni, calculated as NiO, 11% by weight of Cu, calculated as CuO, and 28% by weight of Co, calculated as CoO.

The catalysts or catalyst precursors are preferably used in the form of shaped bodies in the process of the invention.

Suitable shaped bodies are shaped bodies of any geometry or shape. Preferred shaped bodies are tablets, rings, cylinders, star extrudates, wagon wheels or spheres, particularly preferably tablets, rings, cylinders, spheres or star extrudates. Very particular preference is given to the rod shape.

In the case of spheres, the diameter of the sphere is preferably 10 mm or less, particularly preferably 4 mm or less, very particularly preferably 3 mm or less and in particular 2.5 mm or less.

In a preferred embodiment, the diameter of the sphere, in the case of spheres, is preferably in the range from 0.1 to 10 mm, particularly preferably from 0.5 to 4 mm, very particularly preferably from 1 to 3 mm and in particular from 1.5 to 2.5 mm.

In the case of rods or cylinders, the ratio of length:diameter is preferably in the range from 1:1 to 20:1, particularly preferably from 1:1 to 14:1, very particularly preferably in the range from 1:1 to 10:1 and in particular in the range from 1:2 to 6:1.

The diameter of the rods or cylinders is preferably 10 mm or less, particularly preferably 5 mm or less, very particularly preferably 3 mm or less and in particular 2.5 mm or less.

In a preferred embodiment, the diameter of the rods or cylinders is preferably in the range from 0.1 to 10 mm, particularly preferably in the range from 0.5 to 3 mm, very particularly preferably in the range from 1 to 2.5 mm and in particular in the range from 1.5 to 2.5 mm.

In the case of tablets, the height h of the tablet is preferably 10 mm or less, particularly preferably 4 mm or less, very particularly preferably 3 mm or less and in particular 2.5 mm or less.

In a preferred embodiment, the height h of the tablet is preferably in the range from 0.1 to 10 mm, particularly preferably in the range from 0.5 to 4 mm, very particularly preferably in the range from 1 to 3 mm and in particular in the range from 1.5 to 2.5 mm.

The ratio of height h (or thickness) of the tablet to the diameter D of the tablet is preferably from 1:1 to 1:5, particularly preferably from 1:1 to 1:2.5, very particularly preferably from 1:1 to 1:2 and in particular from 1:1 to 1:2.

In the case of all other geometries, the shaped catalyst body used in the process of the invention preferably has, in each case, an equivalent diameter L=1/a' of 2 mm or less, particularly preferably 1 mm or less, very particularly preferably 0.7 mm or less and in particular 0.5 mm or less, where a' is the external surface area per unit volume (mm$_s^2$/mm$_p^3$), where:

$$a' = \frac{A_p}{V_p},$$

where $A_p$ is the external surface area of the shaped body (mm$_s^2$) and $V_p$ is the volume of the shaped body (mm$_p^3$).

In a preferred embodiment, the shaped catalyst body used in the process of the invention has, in the case of all other geometries, in each case preferably an equivalent diameter L=1/a' in the range from 0.1 to 2 mm, particularly preferably in the range from 0.1 to 0.7 mm, very particularly preferably in the range from 0.2 to 0.5 mm and in particular in the range from 0.3 to 0.4 mm.

The surface area and the volume of the shaped body are derived from the geometric dimensions of the shaped body according to the known mathematical formulae.

The volume can also be calculated by the following method, in which:
1. The internal porosity of the shaped body is determined (e.g. by measuring the water uptake in [ml/g of cat] at room temperature and 1 bar total pressure),
2. the displacement of the shaped body on immersion in a fluid (e.g. by gas displacement by means of a helium pycnometer) is determined and
3. the sum of the two volumes is calculated.

The surface area can also be calculated theoretically by the following method in which an envelope around the shaped body whose curve radii are not more than 5 μm (in order not to include the internal pore surface area by "intrusion" of the envelope into the pores) and which contacts the shaped body as closely as possible (no intersection with the support) is defined. This would, for the purposes of illustration, correspond to a very thin film which is placed around the shaped body and a vacuum is then applied from the inside so that the film is very close against the shaped body.

The shaped body used preferably has a bulk density (in accordance with EN ISO 6) in the range from 0.1 to 3 kg/l, preferably from 1.5 to 2.5 kg/l and particularly preferably from 1.7 to 2.2 kg/l.

In a preferred embodiment, the catalysts are used in the process of the invention in the form of shaped bodies which are produced by impregnation of support materials which have the abovementioned geometry or are shaped after impregnation to produce shaped bodies having the abovementioned geometry.

Possible support materials are, for example, carbon such as graphite, carbon black, graphene, carbon nanotubes and/or activated carbon, aluminum oxide (gamma, delta, theta, alpha, kappa, chi or mixtures thereof), silicon dioxide, zirconium dioxide, zeolites, aluminosilicates or mixtures thereof.

The impregnation of the abovementioned support materials can be carried out by customary methods (A. B. Stiles, Catalyst Manufacture—Laboratory and Commercial Preparations, Marcel Dekker, New York, 1983), for example by application of a metal salt solution in one or more impregnation stages. Possible metal salts are generally water-soluble metal salts such as nitrates, acetates or chlorides of the appropriate catalytically active components or doping elements, e.g. Co nitrate or Co chloride. The impregnated support material is then generally dried and optionally calcined.

The calcination is generally carried out at temperatures in the range from 300 to 800° C., preferably from 350 to 600° C., in particular from 450 to 550° C.

The impregnation can also be carried out by the "incipient wetness method", in which the support material is moistened with the impregnation solution to a maximum of saturation according to its water uptake capacity. However, the impregnation can also be carried out with supernatant solution.

In multistage impregnation processes, it is advantageous to dry and optionally calcine the support material between individual impregnation steps. Multistage impregnation is advantageous when a relatively large amount of metal salts is to be applied to the support material. To apply a plurality of metal components to the support material, impregnation can be carried out simultaneously with all metal salts or with the individual metal salts in succession in any order.

Preference is given to using support materials which already have the above-described preferred geometry of the shaped bodies.

However, it is also possible to use support materials which are present as powder or crushed material and subject the impregnated support materials to shaping.

Thus, for example, the impregnated and dried and/or calcined support material can be conditioned.

Conditioning can, for example, be carried out by bringing the impregnated support material to a particular particle size by milling.

After milling, the conditioned, impregnated support material can be mixed with shaping aids such as graphite or stearic acid and processed further to produce shaped bodies. Customary processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

Customary processes for shaping are, for example, extrusion, tableting, i.e. mechanical pressing, or pelletization, i.e. compacting by means of circular and/or rotational movements. Shaped bodies having the abovementioned geometry can be obtained by the shaping process. After conditioning or shaping, the shaped body is generally heat treated. The temperatures in the heat treatment usually correspond to the temperatures in the calcination.

In a preferred embodiment, shaped bodies which are produced by joint precipitation (coprecipitation) of all their components are used in the process of the invention and the catalyst precursors which have been precipitated in this way are subjected to shaping.

For this purpose, a soluble compound of the appropriate active component, the doping elements and optionally a soluble compound of a support material is treated in a liquid, hot and while stirring, with a precipitant until precipitation is complete.

Water is generally used as liquid.

Possible soluble compounds of the active components are usually the corresponding metal salts such as the nitrates, sulfates, acetates or chlorides of the abovementioned metals. As soluble compounds of a support material, use is generally made of water-soluble compounds of Ti, Al, Zr, Si, etc., for example the water-soluble nitrates, sulfates, acetates or chlorides of these elements.

As soluble compounds of the doping elements, use is generally made of water-soluble compounds of the doping elements, for example the water-soluble nitrates, sulfates, acetates or chlorides of these elements.

In a further, preferred embodiment, the shaped bodies can be produced by precipitating on. For the purposes of the present invention, precipitating on is a production method in which a sparingly soluble or insoluble support material is suspended in a liquid and soluble compounds, e.g. soluble metal salts, of the appropriate metal oxides are added and are then precipitated onto the suspended support by addition of a precipitant (e.g. as described in EP-A2-1 106 600, page 4, and A. B. Stiles, Catalyst Manufacture, Marcel Dekker, Inc., 1983, page 15).

Possible sparingly soluble or insoluble support materials are, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present as powder or crushed material.

As liquid in which the support material is suspended, use is usually made of water. Possible soluble compounds are the abovementioned soluble compounds of the active components and the doping elements.

In the precipitation reactions, the soluble compounds are usually precipitated as sparingly soluble or insoluble, basic salts by addition of a precipitant.

As precipitant, preference is given to using alkalis, in particular mineral bases such as alkali metal bases. Examples of precipitants are sodium carbonate, sodium hydroxide, potassium carbonate and potassium hydroxide.

It is also possible to use ammonium salts, for example ammonium halides, ammonium carbonate, ammonium hydroxide or ammonium carboxylates, as precipitants.

The precipitation reactions can be carried out, for example, at temperatures of from 20 to 100° C., particularly preferably from 30 to 90° C., in particular from 50 to 70° C.

The precipitates obtained in the precipitation reactions are generally chemically nonuniform and as a rule comprise mixtures of the oxides, oxide hydrates, hydroxides, carbonates and/or hydrogencarbonates of the metals used. It can prove to be advantageous in terms of the filterability of the precipitates for them to be aged, i.e. for them to be left to stand for some time after the precipitation, optionally hot or with air being passed through.

The precipitates obtained by these precipitation processes are usually processed by washing, drying, calcining and conditioning them.

After washing, the precipitates are generally dried at from 80 to 200° C., preferably from 100 to 150° C., and subsequently calcined.

Calcination is generally carried out at temperatures in the range from 300 to 800° C., preferably from 350 to 600° C., in particular from 450 to 550° C.

After calcination, the pulverulent catalyst precursors obtained by precipitation reactions are usually conditioned.

Conditioning can, for example, be carried out by bringing the precipitated catalyst to a particular particle size by milling.

After milling, the catalyst precursor obtained by precipitation reactions can be mixed with shaping aids such as graphite or stearic acid and processed further to produced shaped bodies.

Customary processes for shaping are described, for example, in Ullmann [Ullmann's Encyclopedia Electronic Release 2000, Chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

Customary processes for shaping are, for example, extrusion, tableting, i.e. mechanical pressing, or pelletization, i.e. compaction by means of circular and/or rotational movements. Shaped bodies having the abovementioned geometry can be obtained by the shaping process. After conditioning or shaping, the shaped body is generally heat treated. The temperatures in the heat treatment usually correspond to the temperatures in the calcination.

Shaped bodies produced by impregnation or precipitation generally comprise the catalytically active components in the form of their oxygen-comprising compounds, for example their metal oxides or hydroxides, e.g. CoO, NiO, CuO and/or mixed oxides thereof (catalyst precursors), after calcination.

The catalyst precursors which have been produced as described above by impregnation or precipitation are generally reduced after calcination or conditioning. The reduction generally converts the catalyst precursor into its catalytically active form.

The reduction of the catalyst precursor can be carried out at elevated temperature in an agitated or unagitated reduction oven.

As reducing agent, it is usual to use hydrogen or a hydrogen-comprising gas.

Technical-grade hydrogen is generally used. The hydrogen can also be used in the form of a hydrogen-comprising gas, i.e. in admixture with other inert gases such as nitrogen, helium, neon, argon or carbon dioxide. The hydrogen stream can also be recirculated as recycle gas to the reduction, optionally mixed with fresh hydrogen and optionally after removal of water by condensation.

The reduction of the catalyst precursor is preferably carried out in a reactor in which the shaped bodies are arranged as a fixed bed. The reduction of the catalyst precursor is particularly preferably carried out in the same reactor in which the subsequent reaction of the nitriles with hydrogen is carried out.

Furthermore, the reduction of the catalyst precursor can be carried out in a fluidized bed in a fluidized-bed reactor.

The reduction of the catalyst precursor is generally carried out at reduction temperatures of from 50 to 600° C., in particular from 100 to 500° C., particularly preferably from 150 to 450° C.

The hydrogen partial pressure is generally from 1 to 300 bar, in particular from 1 to 200 bar, particularly preferably from 1 to 100 bar, with the pressures indicated here and in the following being the absolute pressure measured.

The duration of the reduction is preferably from 1 to 20 hours and particularly preferably from 5 to 15 hours.

During the reduction, a solvent can be introduced in order to remove the water of reaction formed and/or to be able, for example, to heat the reactor more quickly and/or to be able to remove the heat more readily during the reduction. The solvent can here also be introduced in supercritical form.

Suitable solvents which can be used are the above-described solvents. Preferred solvents are water; ethers such as methyl tert-butyl ether, ethyl tert-butyl ether, dioxane or tetrahydrofuran. Particular preference is given to water or tetrahydrofuran. Suitable mixtures are likewise possible as suitable solvents.

The shaped body obtained in this way can be handled under inert conditions after the reduction. The shaped body can preferably be handled and stored under an inert gas such as nitrogen or under an inert liquid, for example an alcohol, water or the product of the respective reaction for which the catalyst is used. The catalyst may then have to be freed of the inert liquid before commencement of the actual reaction.

Storage of the catalyst under inert substances makes uncomplicated and nonhazardous handling and storage of the shaped body possible.

However, the shaped body can, after reduction, also be brought into contact with an oxygen-comprising gas stream such as air or a mixture of air with nitrogen.

A passivated shaped body is obtained as a result. The passivated shaped body generally has a protective oxide layer. This protective oxide layer simplifies handling and storage of the catalyst, so that, for example, installation of the passivated shaped body in the reactor is simplified. A passivated shaped body is preferably reduced as described above by treatment of the passivated catalyst with hydrogen or a hydrogen-comprising gas before being brought into contact with the starting materials. The reduction conditions generally correspond to the reduction conditions employed in the reduction of the catalyst precursors. The protective passivation layer is generally removed by the activation.

The process of the invention is preferably carried out in a reactor in which the catalyst is arranged as a fixed bed.

In a preferred embodiment, the fixed-bed arrangement comprises a catalyst bed in the true sense, i.e. loose, supported or unsupported shaped bodies which preferably have the above-described geometry or shape.

For this purpose, the shaped bodies are introduced into the reactor.

For the shaped bodies to remain in the reactor and not fall through the latter, a mesh or a gas- and liquid-permeable metal plate on which the shaped bodies rest is usually used.

The shaped bodies can be surrounded by an inert material both at the inlet to or the outlet from the reactor. As inert material, use is generally made of shaped bodies which have a similar geometry to that of the above-described shaped catalyst bodies but are inert in the reaction, e.g. Pall rings, spheres of an inert material (e.g. ceramic, steatite, aluminum).

However, the shaped bodies can also be mixed with inert material and be introduced as a mixture into the reactor.

The catalyst bed (shaped bodies+optionally inert material) preferably has a bulk density (in accordance with EN ISO 6) in the range from 0.1 to 3 kg/l, preferably from 1.5 to 2.5 kg/l and particularly preferably from 1.7 to 2.2 kg/l.

The differential pressure over the bed is preferably less than 1000 mbar/m, preferably less than 800 mbar/m and particularly preferably less than 700 mbar/m. The differential pressure over the bed is preferably in the range from 10 to 1000 mbar/m, preferably from 50 to 800 mbar/m, particularly preferably from 100 to 700 mbar/m and in particular in the range from 200 to 500 mbar/m.

In the downflow mode (flow direction of the liquid from the top downward), the differential pressure is derived from the pressure measured above the catalyst bed and the pressure measured below the catalyst bed.

In the upflow mode (flow direction of the liquid from the bottom upward), the differential pressure is derived from the pressure measured below the catalyst bed and the pressure measured above the catalyst bed.

Suitable fixed-bed reactors are described, for example, in the article "Fixed-Bed Reactors" (Ullmann's Encyclopedia of Industrial Chemistry, Published Online: 15 Jun. 2000, DOI: 10.1002/14356007. b04_199).

The process is preferably carried out in a shaft reactor, shell-and-tube reactor or tube reactor.

The process is particularly preferably carried out in a tube reactor.

The reactors can in each case be used as a single reactor, as a series of individual reactors and/or in the form of two or more parallel reactors.

The specific reactor construction and the way in which the reaction is carried out can vary as a function of the hydrogenation process to be carried out, the reaction times required and the nature of the catalyst used.

The ratio of height to diameter of the reactor, in particular a tube reactor, is preferably from 1:1 to 500:1, particularly preferably from 2:1 to 100:1 and in particular from 5:1 to 50:1.

The flow direction of the reactants (starting materials, hydrogen, optionally liquid ammonia) is generally from the top downward or from the bottom upward.

The flow direction of the reactants (starting materials, hydrogen, optionally liquid ammonia) is particularly preferably from the top downward through the reactor.

The space velocity over the catalyst in continuous operation is typically from 0.01 to 10 kg, preferably from 0.2 to 5 kg, particularly preferably from 0.2 to 4 kg, of starting material per l of catalyst and hour.

The cross-sectional loading is, according to the invention, in the range from 5 kg/(m² s) to 50 kg/(m² s), preferably from 8 to 25 kg/(m² s), particularly preferably from 10 to 20 kg/(m² s) and in particular from 12 to 18 kg/(m² s).

The cross-sectional loading v [kg/(m² s)] is defined as $$v = \frac{Q}{A},$$

where Q is the mass flow rate [kg/s] and A is the cross-sectional area of the empty column [m²]. The mass flow rate Q is in turn defined as the sum of the masses of all feed streams and recycle streams introduced. Hydrogen, recycle gases and any inert gases introduced are not used for calculating the mass flow rate since hydrogen, recycle gases and inert gases are generally present in the gas phase under the usual hydrogenation conditions.

To achieve high cross-sectional loadings, part of the output (part output) from the hydrogenation reactor is recirculated as a recycle stream to the reactor (circulating stream). The recirculated stream can be fed separately into the reactor or can particularly preferably be mixed with the starting materials fed in and fed back together with these into the reactor.

The ratio of circulating stream to feed stream fed in is preferably in the range from 0.5:1 to 250:1, particularly preferably in the range from 1:1 to 200:1 and in particular in the range from 2:1 to 180:1. If no ammonia is introduced into the process, the ratio of circulating stream to feed stream fed in is preferably in the upper region of the abovementioned ranges. On the other hand, if a large amount of ammonia is introduced into the process, the ratio of circulating stream to feed stream fed in is preferably in the lower region of the abovementioned ranges.

In a further preferred embodiment, high cross-sectional loadings can be achieved when the reaction is carried out in a reactor having a slim construction, in particular in a tube reactor having a slim construction.

The ratio of height to diameter of the reactor is therefore, as described above, preferably in the range from 1:1 to 500:1, particularly preferably in the range from 2:1 to 100:1 and in particular in the range from 5:1 to 50:1.

The hydrogenation is generally carried out at a pressure of from 1 to 200 bar, in particular from 5 to 150 bar, preferably from 10 to 100 bar and particularly preferably from 15 to 95 bar. The hydrogenation is very particularly preferably carried out at a pressure of less than 95 bar as low-pressure process.

The temperature is generally in the range from 25 to 300° C., in particular from 50 to 200° C., preferably from 70 to 150° C., particularly preferably from 80 to 140° C.

The reaction conditions are preferably selected so that the nitriles used and any liquids added and any ammonia introduced are generally present in the liquid phase and only the hydrogen or inert gases used are present in the gas phase under the stated reaction conditions.

The molar ratio of hydrogen to nitrile used is generally from 2:1 to 25:1, preferably from 2.01:1 to 10:1. The hydrogen can be returned as recycle gas to the reaction.

In the process of the invention for preparing amines by reduction of nitriles, the hydrogenation can be carried out with addition of ammonia. Ammonia is generally added in molar ratios to the nitrile group of from 0.5:1 to 100:1, preferably from 2:1 to 20:1. However, the preferred embodiment is a process in which no ammonia is added.

The reaction can be carried out in bulk or in a liquid.

The hydrogenation is preferably carried out in the presence of a liquid.

Suitable liquids are, for example, C1-C4-alcohols such as methanol or ethanol, C4-C12-dialkyl ethers such as diethyl ether or tert-butyl methyl ether or cyclic C4-C12-ethers such as tetrahydrofuran or dioxane or hydrocarbons such as pentane, hexane, heptane, octane, cyclohexane or toluene. Suitable liquids can also be mixtures of the abovementioned liquids. In a preferred embodiment, the liquid is a product of the hydrogenation.

The reaction can also be carried out in the presence of water. However, the water content should be not more than 10% by weight, preferably less than 5% by weight, particularly preferably less than 3% by weight, based on the mass of the liquid used, in order to very largely avoid leaching and/or washing off of the compounds of the alkali metals, alkaline earth metals and/or rare earth metals.

The activity and/or selectivity of the catalysts according to the invention can decrease with an increasing period of operation. We have accordingly found a process for regenerating the catalysts according to the invention, in which the catalyst is treated with a liquid. The treatment of the catalyst with a liquid should lead to any adhering compounds which block active sites of the catalyst being dissolved off. The treatment of the catalyst with a liquid can be effected by stirring the catalyst in a liquid or by washing the catalyst with the liquid; after the treatment is complete, the liquid can be separated off together with the dissolved-off impurities from the catalyst by filtration or decantation.

Suitable liquids are as a rule the product of the hydrogenation, water or an organic solvent, preferably ethers, alcohols or amides.

In a further embodiment, the treatment of the catalyst with liquid can be carried out in the presence of hydrogen or a hydrogen-comprising gas.

This regeneration can be carried out at elevated temperature, in general from 20 to 250° C. It is also possible to dry the used catalyst and oxidize adhering organic compounds to volatile compounds such as $CO_2$ by means of air. Before further use of the catalyst in hydrogenation, the catalyst generally has to be activated as described above after oxidation.

In the regeneration, the catalyst can be brought into contact with a soluble compound of the catalytically active components. Contacting can be carried out in such a way that the catalyst is impregnated or wetted with a water-soluble compound of the catalytically active component.

In the hydrogenation of nitriles to the corresponding amines, it is frequently necessary to achieve a high conversion of the nitriles used since unreacted or only partially reacted nitriles can be removed only with difficulty and can lead to undesirable properties such as odor and discoloration in subsequent applications.

The advantage of the present invention is that the process of the invention makes the hydrogenation of nitriles in high selectivity and yield possible. In addition, the formation of undesirable by-products is reduced.

As a result, it is possible to carry out the hydrogenation under milder reaction conditions, in particular at lower pressure and/or at lower temperature.

Thus, the present invention makes an economical hydrogenation process possible. In particular, the formation of secondary and tertiary amines as can be formed, for example, by reaction of unreacted amine with partially hydrogenated nitrile (=imine intermediate) as shown in scheme 1.

In particular, the process of the invention makes it possible to prepare isophoronediamine in high selectivity and yield. In particular, it is possible to reduce the content of undesirable isophoronenitrilamine (IPNA). IPNA can, for example, be formed by reaction of isophoronenitrile with ammonia which firstly reacts to form isophoronenitrilimine, which then preferentially reacts with hydrogen to form isophoronenitrilamine.

Isophoronediamine serves as intermediate for the production of hardeners for epoxy resins and coatings (e.g. 3-isocyanatomethyl-3,5,5-trimethylcyclohexyl isocyanate) and is itself also used directly as hardener. Further applications are coatings having excellent corrosion protection properties for metals and adhesive compounds. Furthermore, it is used in the preparation of noncrystalline specialty polyamides, as chain extender in polyurethanes and as intermediate for the production of dyes.

The present invention thus also provides a process for preparing hardeners for epoxy resins and coatings, specialty polyamides, polyurethanes and dyes, wherein isophoronediamine is prepared from isophoronenitrilimine according to claim 1 in a first stage and the isophoronediamine obtained in the first stage is used in a second stage for preparing hardeners for epoxy resins and coatings, specialty polyamides, polyurethanes and dyes.

Owing to the low content of IPNA, the downstream products can also have advantageous properties.

The process of the invention is likewise preferred for preparing 3-(dimethylamino)propylamine (DMAPA). In particular, the process of the invention makes it possible to reduce the content of bis-DMAPA. This is used, for example, as intermediate for producing surface-active substances, soaps, cosmetics, shampoos, hygiene products, detergents and crop protection agents. DMAPA is also used for water treatment and as polymerization catalyst for PU and epoxy.

The present invention therefore also provides a process for producing surface-active substances, soaps, cosmetics, shampoos, hygiene products, detergents and crop protection agents, wherein DMAPA is prepared from 3-(dimethylamino)propionitrile according to claim 1 in a first stage and the DMAPA obtained in the first stage is used in a second stage for producing surface-active substances, soaps, cosmetics, shampoos, hygiene products, detergents and crop protection agents.

Owing to the low content of bis-DMAPA, the downstream products can also have advantageous properties.

The invention is illustrated by the following examples:

EXAMPLES

Definitions:

The space velocity of the catalyst is reported as the quotient of the mass of starting material in the feed and the product of catalyst volume and time.

Space velocity of the catalyst=mass of starting material/(volume of catalyst·reaction time).

The unit of the space velocity of the catalyst is $[kg_{starting\ material}/(l\cdot h)]$.

The selectivities reported were determined by gas-chromatographic analyses and were calculated from the percentages by area.

GC Programs:

IPDA: GC column: 60 m DB1701; ID=0.32 mm, film thickness=0.25 μm

Temperature program: 60° C.—5° C./min—280° C.—20 min

DMAPA: GC column: 60 m CP Volamnin; WCOT Fused Silica 0.32 mm

Temperature program: 50° C.—10 min—15° C./min—240° C.—30 min

The starting material conversion U(E) is calculated according to the following formula:

$$U(E) = \frac{F\ \%\ (E)_{beginning} - F\ \%\ (E)_{end}}{F\ \%\ (E)_{beginning}}$$

The yield of product A(P) is derived from the percentages by area of the product signal $$A(P)=F\ \%(P),$$

where the percentages by area F %(i) of a starting material (F % (E)), product (F %(P)), a by-product (F %(N)) or quite generally a material i (F %(i)) is given by the quotient of the area F(i) under the signal of the material i and the total area $F_{total}$, i.e. the sum of the area under the signal i, multiplied by 100:

$$F\ \%\ (i) = \frac{F(i)}{F_{total}}\cdot 100 = \frac{F(i)}{\sum_i F(i)}\cdot 100$$

The selectivity of the starting material S(E) is given by the quotient of product yield A(P) and starting material conversion U(E):

$$S(E) = \frac{A(P)}{U(E)}*100$$

Production of the Catalyst

As catalyst, use was made of a cobalt catalyst having a rod diameter of 2 mm, the production of which is described in EP-A-0636409 (illustrative catalyst A).

Example 1

Conversion of IPN into IPDA

The reaction was carried out in two continuously operated tube reactors connected in series. Here, the imination of isophoronenitrile (IPN) by means of ammonia to give isophoronenitrilimine (IPNI) was carried out in the first reactor at 60° C. over TiO$_2$ (75 ml). The feed rate of IPN was 84 g/h, and the feed rate of NH$_3$ was 180 g/h. The output from the imination reactor was passed together with hydrogen to the second reactor. The temperature of the second reactor was set to 90° C. The amount of hydrogen introduced was 88 l/h. 180 ml of the previously activated cobalt catalyst were used as catalyst. The hydrogenation reactor had an internal cross section of 16 mm, with a temperature sensor sheath having an external diameter of 3.7 mm being installed in the reactor. The proportion of aminonitrile (IPNA) in the output from the hydrogenation reactor at various recycle streams was determined (see table 1). The liquid recirculation reported is the ratio of the recycle stream to the sum of IPN and ammonia fed in. Table 1 shows IPNA and IPDA values as various recycle:feed ratios and pressures. For this purpose, the cross-sectional loading (QB) was calculated for each of the settings. The percentages are GC % by area.

TABLE 1

| | | Values after the hydrogenation | | |
|---|---|---|---|---|
| Pressure | Recycle:Feed | IPNA | IPDA | Cross-sectional loading |
| 80 bar | 10:1 | 24% | 62% | 4.2 kg/m$^2$/s |
| 80 bar | 20:1 | 8% | 85% | 8.1 kg/m$^2$/s |
| 80 bar | 40:1 | 7% | 87% | 15.8 kg/m$^2$/s |
| 70 bar | 10:1 | 19% | 73% | 4.2 kg/m$^2$/s |
| 70 bar | 40:1 | 7% | 85% | 15.8 kg/m$^2$/s |

It can be seen from the table that at relatively high recycle streams, the proportion of IPNA and thus partially hydrogenated product surprisingly decreases while the proportion of IPDA increases. This finding is surprising because stirred tank characteristics of the tube reactor would have been expected at very high recycle rates. As a result of this, the proportion of unhydrogenated components in the output should increase. Thus, at 80 bar, increasing the recycle flow and thus increasing the cross-sectional loading reduces the proportion of IPNA from an initial 24% at 4.2 kg/m$^2$/s to 7% at 15.8 kg/m$^2$/s. At the same time, the proportion of IPDA increases correspondingly (62% or 87%). This effect is also observed at 70 bar: here, the proportion of IPNA decreases from an initial 19% at a QB of 4.2 kg/m$^2$/s to 7% at a QB of 15.8 kg/m$^2$/s, and the proportion of IPDA increases from 73% to 85%.

Example 2

Conversion of DMAPN into DMAPA

The reaction was carried out in a tube reactor (internal diameter: 0.6 cm, length: 1 m) with liquid recirculation at 90° C. and 85 bar in the presence of hydrogen and ammonia. The reactor was charged with 40.2 g of cobalt catalyst. Before commencement of the reaction, the reduced passivated cobalt catalyst was reduced in a stream of hydrogen at 280° C. (1 bar) for 12 hours and started up using DMAPA. The reactor was subsequently cooled to the desired reaction temperature and pressurized with 85 bar of hydrogen. Before switching the feed over to DMAPN, the liquid recirculation and the introduction of ammonia was set.

The feed rate of DMAPN was initially 19.4 g/h, and the NH$_3$ feed rate was 19 g/h. The amount of hydrogen fed in was 25 l/h. A recycle rate of liquid from the hydrogenation output of 40 g/h was set (cf. 1) table 2). The cross-sectional loading (QB) was increased by a factor of 10 by increasing the amount of liquid recirculated and increasing the recycle ratio (recycle:feed) under otherwise constant reaction conditions. The undesirable formation of bisDMAPA was completely suppressed by the increased QB (cf. 2) table 2).

Example 3

Conversion of DMAPN into DMAPA

The reaction was carried out in a tube reactor (internal diameter: 0.5 cm, length: 1 m, cross-sectional area: 0.196 cm$^3$) through which flow occurred from the top downward, at 90° C. and 85 bar in the presence of hydrogen and with recirculation of liquid. Before commencement of the reaction, 24.5 g of the reduced passivated cobalt catalyst (production: commercially available lithium-cobalt(III) oxide from Aldrich ("lithium cobaltite", LiCoO$_2$) were extruded with addition of 25% of zinc oxide powder and dilute nitric acid, polyethylene oxide and Acronal V312 to form 4 mm shaped bodies; then reduction at 300° C./1 bar in a stream of hydrogen, then passivation) were installed in the reactor and activated at 300° C. (1 bar) in a stream of hydrogen (25 standard l/h) for 12 hours. The reactor was subsequently cooled to the initial reaction temperature of 150° C., pressurized with 85 bar of hydrogen and started up using DMAPA. A hydrogen flow of 50 standard l/h was set. A recirculation of liquid of 934 g/h was set. The feed rate of DMAPN was 6 g/h (corresponding to a cross-sectional loading (QB) of 13.32 kg/m$^2$/s). The conversion of DMAPN was 99%, and the amount of bisDMAPA formed was 0.1%. The recirculation of liquid was subsequently set to a lower value of 63 g/h. Under otherwise constant reaction conditions, this reduced the QB by a factor of 15 (corresponding to QB of 0.98 kg/m$^2$/s). At a constant high conversion of 99%, only 0.8% of bisDMAPA was now found in the reaction output.

The invention claimed is:

1. A process comprising hydrogenating nitriles by means of hydrogen in the presence of a catalyst in a reactor, where the catalyst is arranged in a fixed bed, wherein the cross-sectional loading in the reactor is in the range from 5 kg/(m$^2$ s) to 50 kg/(m$^2$ s);
    wherein isophoronenitrilimine or 3-(dimethylamino)propionitrile is used as nitrile; and
    wherein the catalyst comprises a reduced passivated cobalt catalyst.

2. The process according to claim 1, wherein the fixed bed is a catalyst bed made up of loose, supported or unsupported shaped bodies.

3. The process according to claim 2, wherein the shaped bodies are used in the form of tablets, rings, cylinders, spheres or star extrudates.

4. The process according to claim 2, wherein the shaped body
    in the case of spheres has a diameter of the sphere of from 0.1 to 10 mm or

TABLE 2

| | | | | DMAPA | | | | | |
|---|---|---|---|---|---|---|---|---|---|
| | Pressure [bar] | Temp. [° C.] | Space velocity [kg/l * h] | DMAPN [g/h] | Recycle:Feed [g/h:g/h] | QB [kg/m$^2$/s] | Conversion [% by area] | BisDMAPA [% by area] | DMAPA [% by area] |
| 1) | 85 | 90 | 1.00 | 19.4 | 2.1 | 0.77 | 100.00 | 0.87 | 99.13 |
| 2) | 85 | 90 | 1.00 | 19.4 | 38.5 | 7.77 | 99.75 | 0.00 | 99.75 | in the case of rods or cylinders the ratio of length:diameter is in the range from 2:1 to 20:1 and the diameter is from 0.1 to 10 mm or in the case of tablets the diameter D of the tablet is in the range from 1 to 10 mm and the ratio of height h of the tablet to diameter is in the range from 1:1 to 1:5 or in the case of all other geometries the shaped body has an equivalent diameter L=1/a' of from 0.1 to 2 mm, where a' is the external surface area per unit volume ($mm_s^2/mm_p^3$), where $$a' = \frac{A_p}{V_p},$$

where $A_p$ is the external surface area of the shaped body ($mm_s^2$) and $V_p$ is the volume of the shaped body ($mm_p^3$).

5. The process according to claim 1, wherein the bulk density of the bed is from 0.1 to 3 kg/l.

6. The process according to claim 1, wherein the catalyst is produced by reduction of catalyst precursors.

7. The process according to claim 1, wherein part of the output (part output) from the hydrogenation reactor is recirculated as recycle stream to the reactor (circulating stream) and the ratio of circulating stream to feed stream fed in is in the range from 0.5:1 to 250:1.

8. The process according to claim 1, wherein the pressure is in the range from 15 to 85 bar and/or the temperature is in the range from 70 to 150° C.

9. The process according to claim 1, wherein the process is carried out in a shaft reactor, tube reactor or shell-and-tube reactor.

10. The process according to claim 9, wherein the ratio of height to diameter of the tube reactor is from 1:1 to 500:1.

11. The process according to claim 1, wherein the differential pressure over the catalyst bed is less than 1000 mbar/m.

12. A process for preparing hardeners for epoxy resins and coatings, specialty polyamides, polyurethanes, and dyes, said process comprising preparing isophoronediamine according to the process of claim 1 from isophoronenitrilimine, and preparing the hardeners from the isophoronediamine.

13. A process for producing surface-active substances, soaps, cosmetics, shampoos, hygiene products, detergents, and crop protection agents, said process comprising preparing N,N-dimethylaminopropylamine according to the process of claim 1 from 3-(dimethylamino)propionitrile, and producing the surface-active substances, soaps, cosmetics, shampoos, hygiene products, detergents, and crop protection agents from the N,N-dimethylaminopropylamine.

* * * * *